US008722112B2

(12) United States Patent  (10) Patent No.: US 8,722,112 B2
Zicker et al.  (45) Date of Patent: May 13, 2014

(54) METHOD FOR PROLONGING THE LIFE OF ANIMALS

(75) Inventors: Steven Curtis Zicker, Lawrence, KS (US); Karen Joy Wedekind, St. Peters, MO (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 11/995,584

(22) PCT Filed: Jul. 14, 2006

(86) PCT No.: PCT/US2006/027615
§ 371 (c)(1),
(2), (4) Date: Aug. 18, 2008

(87) PCT Pub. No.: WO2007/009111
PCT Pub. Date: Jan. 18, 2007

(65) Prior Publication Data
US 2009/0155393 A1 Jun. 18, 2009

Related U.S. Application Data

(60) Provisional application No. 60/699,145, filed on Jul. 14, 2005.

(51) Int. Cl.
*A61K 36/752* (2006.01)

(52) U.S. Cl.
USPC .......................................................... 424/736

(58) Field of Classification Search
None
See application file for complete search history.

(56) References Cited

U.S. PATENT DOCUMENTS

| | | | |
|---|---|---|---|
| 4,006,266 A | 2/1977 | Bone et al. | |
| 4,247,562 A | 1/1981 | Bernotavicz | |
| 4,883,672 A | 11/1989 | Shug et al. | |
| 5,006,361 A | 4/1991 | Cox | |
| 5,030,458 A | 7/1991 | Shug et al. | |
| 5,118,505 A | 6/1992 | Koltringer | |
| 5,292,538 A | 3/1994 | Paul et al. | |
| 5,339,771 A | 8/1994 | Axelrod | |
| 5,419,283 A | 5/1995 | Leo | |
| 5,569,670 A | 10/1996 | Weischer et al. | |
| 5,599,835 A | 2/1997 | Fischer | |
| 5,621,117 A | 4/1997 | Bethge et al. | |
| 5,728,735 A | 3/1998 | Ulrich et al. | |
| 5,730,988 A | 3/1998 | Womack | |
| 5,851,573 A | 12/1998 | Lepine et al. | |
| 5,883,083 A | 3/1999 | Harless | |
| 5,894,029 A | 4/1999 | Brown et al. | |
| 5,916,912 A | 6/1999 | Ames et al. | |
| 5,937,790 A | 8/1999 | Ito et al. | |
| 5,976,568 A | 11/1999 | Riley | |
| 5,977,162 A | 11/1999 | Seidman | |
| 5,981,767 A | 11/1999 | Tanner et al. | |
| 6,080,788 A | 6/2000 | Sole et al. | |
| 6,117,477 A | 9/2000 | Paluch | |
| 6,190,591 B1 | 2/2001 | van Lengerich | |
| 6,232,346 B1 | 5/2001 | Sole et al. | |
| 6,335,361 B1 | 1/2002 | Hamilton | |
| 6,365,211 B1 | 4/2002 | Corrigan | |
| 6,379,727 B1 | 4/2002 | Addy | |
| 6,426,362 B1 | 7/2002 | Miller et al. | |
| 6,479,069 B1 | 11/2002 | Hamilton | |
| 6,572,888 B2 | 6/2003 | Byrd | |
| 6,669,975 B1 | 12/2003 | Abene et al. | |
| 6,914,071 B2 | 7/2005 | Zicker et al. | |
| 7,282,225 B1 | 10/2007 | Davis et al. | |
| 2001/0028896 A1 | 10/2001 | Byrd | |
| 2001/0043983 A1 | 11/2001 | Hamilton | |
| 2001/0044448 A1 | 11/2001 | Dib | |
| 2002/0006907 A1 | 1/2002 | Gardiner et al. | |
| 2002/0076469 A1* | 6/2002 | Zicker et al. | 426/72 |
| 2002/0076470 A1 | 6/2002 | Zicker et al. | |
| 2002/0115710 A1 | 8/2002 | Zicker et al. | |
| 2002/0119182 A1 | 8/2002 | Zicker et al. | |
| 2003/0035821 A1 | 2/2003 | Heaton et al. | |
| 2003/0044466 A1 | 3/2003 | Markey et al. | |
| 2003/0060503 A1 | 3/2003 | Hamilton | |
| 2003/0224061 A1 | 12/2003 | Pacioretty et al. | |
| 2004/0047896 A1 | 3/2004 | Malnoe et al. | |
| 2004/0068010 A1 | 4/2004 | Zicker et al. | |
| 2004/0166157 A1 | 8/2004 | Thombre | |
| 2005/0100617 A1 | 5/2005 | Malnoe et al. | |
| 2005/0123628 A1 | 6/2005 | Zabrecky | |
| 2005/0123643 A1 | 6/2005 | Cupp et al. | |
| 2008/0317725 A1 | 12/2008 | Baum | |
| 2009/0176864 A1 | 7/2009 | Zicker et al. | |

FOREIGN PATENT DOCUMENTS

| | | |
|---|---|---|
| CA | 2285490 | 4/2001 |
| CA | 2427692 | 5/2002 |
| CA | 2427261 | 6/2002 |
| CN | 1323165 A | 11/2001 |

(Continued)

OTHER PUBLICATIONS

Head et al. A Longitudinal Dietary Antioxidant Intervention in Aged Canines Improves Learning and Reduces Peripheral Measures of Oxidative Damage. abstract from 32nd Annual Meeting of the Society for Neuroscience. 2002.*
Austed. Aging Cell. 2008. 7. pp. 119-124.*
Blagosklonny. An Anti-Aging Drug Today: From Senescence-Promoting Genes to Anti-Aging Pill. Drug Discovery Today. Volume 12, Nos. 5/6. Mar. 2007. pp. 218-224.*
Dogs and Cats-Different Species, Different Needs. Retrieved from the internet. <http://www.felinefuture.com/?p=521>. Retrieved on Nov. 16, 2009. pp. 1-4.*

(Continued)

*Primary Examiner* — Amy L Clark
(74) *Attorney, Agent, or Firm* — Thomas M. Hunter

(57) ABSTRACT

A method for increasing the longevity of an old animal comprising administering to the animal a composition comprising one or more antioxidants in a total antioxidant amount sufficient to increase the longevity of the animal.

13 Claims, No Drawings

(56) References Cited

FOREIGN PATENT DOCUMENTS

| CN | 1829448 A | 9/2006 |
|---|---|---|
| CN | 101107012 | 1/2008 |
| DE | 19818563 | 10/1999 |
| EP | 0427247 | 5/1991 |
| EP | 1118332 | 7/2001 |
| EP | 1247456 | 10/2002 |
| EP | 1637041 | 3/2006 |
| EP | 1339292 | 12/2009 |
| JP | H2-49723 A | 2/1990 |
| JP | H10-042798 A | 2/1998 |
| JP | 2003-052338 A | 2/2003 |
| JP | 2003-261456 A | 9/2003 |
| JP | 2003-529347 | 10/2003 |
| JP | 2004-512053 | 4/2004 |
| JP | 2004-519241 | 7/2004 |
| JP | 2006-219467 | 8/2006 |
| JP | 2007-062326 | 3/2007 |
| JP | 2007-062332 | 3/2007 |
| JP | 2007-308468 | 11/2007 |
| JP | 2008-063234 | 3/2008 |
| JP | 2008-280322 A | 11/2008 |
| RU | 2071319 | 1/1997 |
| RU | 2099078 | 12/1997 |
| RU | 2303373 | 7/2007 |
| WO | WO 94/02036 | 2/1994 |
| WO | WO 98/04361 | 2/1998 |
| WO | WO 98/41113 | 9/1998 |
| WO | WO 98/43617 | 10/1998 |
| WO | WO 98/57627 | 12/1998 |
| WO | WO 99/66913 | 12/1999 |
| WO | WO 00/02553 | 1/2000 |
| WO | WO 00/11968 | 3/2000 |
| WO | WO 00/30666 | 6/2000 |
| WO | WO 00/44375 | 8/2000 |
| WO | WO 00/48594 | 8/2000 |
| WO | WO 00/49891 | 8/2000 |
| WO | WO 01/17366 | 3/2001 |
| WO | WO 01/21208 | 3/2001 |
| WO | WO 01/58271 | 8/2001 |
| WO | 02/35943 A | 5/2002 |
| WO | WO 02/45525 | 6/2002 |
| WO | WO 02/052955 | 7/2002 |
| WO | WO 02/071874 | 9/2002 |
| WO | WO 03/035056 | 5/2003 |
| WO | 2005/006877 A | 1/2005 |
| WO | WO 2005/013714 | 2/2005 |
| WO | WO 2005/058064 | 6/2005 |
| WO | WO 2006/058248 | 6/2006 |
| WO | WO 2006/058278 | 6/2006 |
| WO | WO 2006/069241 | 6/2006 |
| WO | WO 2006/071919 | 7/2006 |
| WO | WO 2006/074089 | 7/2006 |
| WO | WO 2007/009111 | 1/2007 |
| WO | WO 2007/022344 | 2/2007 |
| WO | WO 2007/063095 | 6/2007 |
| WO | WO 2007/094669 | 8/2007 |
| WO | WO 2007/149815 | 12/2007 |
| WO | WO 2008/151131 | 12/2008 |
| WO | WO 2010/083409 | 7/2010 |
| ZA | 9605149 A | 1/1997 |

OTHER PUBLICATIONS

Hawthorne. Nutritional Requirements of Aging Dogs and Cats. Waltham Focus. 2002. pp. 1-2.*

Milgramet al. Acetyl -L -Carnitine and Alpha Lipoic Acid Supplementation of Aged Beagle Dogs Improves Learning in Two Landmark Discrimination Tests. The FASEB Journal. vol. 21. Nov. 2007. pp. 3756-3762.*

Dunn. Cats Are Different. retrieved from the internet. <http://www.catsofaustralia.com/cat-nutrition.htm.>. Retrieved on Nov. 16, 2009. p. 104.*

Hill et al. Lipoic Acid is 10 Times More Toxic in Cats Than Reported in Humans, Dogs or Rats. J. Anim. Physiol. a. Anim. Nutr. 88. (2004) 150-156.*

Head, E. et al., "A Longitudinal Dietary Antioxidant Intervention in Aged Canines Improves Learning and Reduces Peripheral Measures of Oxidative Damage," BIOSIS, (Jan. 1, 1900) XP002461957.

Ikeda-Douglass, C.J. et al. "Prior Experience, Antioxidants, and Mitochondrial Cofactors Improve Cognitive Function in Aged Beagles," Veterinary Therapeutics, Veterinary Learning Systems, (Jan. 1, 2004) pp. 5-16, XP008092011 Trenton, NJ ISSN: 1528-3593.

Siwak, C.T.. et al., "Chronic antioxidant and mitochondrial cofactor administration improves discrimination learning in aged but not young dogs," Progress in Neuro-Psychopharmacology & Biological Psychiatry, (Mar. 1, 2005) pp. 461-469, 29:3 XP004809116 Oxford, GB ISSN: 0278-5846.

Savitha, S. et al., "Oxidative stress on mitochondrial antioxidant defense system in the aging process: Role of dl-alpha-lipoic acid and l-carnitine," Clinica Chimica Acta, (May 1, 2005) pp. 173-180, 355:1-2 XP004835640 Elsevier BV ISSN: 0009-8981.

European Search Report EP 06 77 4663 mailed May 6, 2009.

AAFCO, 2003, Official Publication of the American Association of Feed Control Officials, p. 220.

AAFCO, 2004, American Association of Feed Control Officials Official Publication pp. 129-137.

Aksenova et al., 1999, "Oxidation of cytosolic proteins and expression of creatine kinase BB in frontal lobe in different neurodegenerative disorders," Dement. Geriatr. Cogn. Disord. 10(2):158-165.

Amazon.com, 2007, "Hill's Science Diet Canine Senior" www.amazon.com website.

Ames et al., 1993, "Oxidants, Antioxidants and the Degenerative Diseases of Aging," Proc. Natl. Acad. Sci. 90(17):7915-7922.

Ames, 1998, "Micronutrients Prevent Cancer and Delay Aging," Toxicol. Lett. 102-103:5-18.

Arivazhagan et al., 2000, "Antioxidant Lipoate and Tissue Antioxidants in Aged Rats," J. Nutr. Biochem. 11(3):122-127.

Arivazhagan et al., 2001, "Effect of DL-α-Lipoic Acid on the Status of Lipid Peroxidation and Antioxidants in Mitochondria of Aged Rats," J. Nutr. Biochem. 12:2-6.

Beckman et al., 1998, "Mitochondrial Aging: Open Questions," Annals NY Acad. Sci. 854:118-127.

Beckman et al., 1998, "The Free Radical Theory of Aging Matures," Physiol. Rev. 78(2):547-581.

Berkson, 1999, "A conservative triple antioxidant approach to the treatment of hepatitis C. Combination of alpha lipoic acid (thioctic acid), silymarin, and selenium: three case histories," Med. Klin 94(Suppl. 3):84-89 Medline AN: NLM10554539 Abstract.

Bezlepkin et al., 1996, "The prolongation of survival in mice by dietary antioxidants depends on their age by the start of feeding this diet," Mech. Ageing Dev. 92(2-3):227-234.

Bickford et al., 2000, "Antioxidant-rich diets improve cerebellar physiology and motor learning in aged rats," Brain Res. 866(1-2):211-217.

Borras et al., 1999, "Age-related changes in the brain of the dog," Vet. Pathol. 36(3):202-211.

Branam, 1987, "Dietary Management of Geriatric Dogs and Cats," Vet. Tech. Vet. Learning Syst. 8(10):501-503.

Brigelius-Flohe et al., 1999, "Vitamin E: Function and Metabolism," FASEB J. 13:1145-1155.

Bruce-Keller et al., 1998, "4-Hydroxynonenal, a product of lipid peroxidation, damages cholinergic neurons and impairs visuospatial memory in rats," J. Neuropathol. And Exp. Neurol. 57(3):257-267.

Cantuti-Castelvetri et al., 2000, "Neurobehavioral Aspects of Antioxidants in Aging," Int. J. Develop. Neurosci. 18(4-5):367-381.

Cao et al., 1998, "Increases in Human Plasma Antioxidant Capacity after Consumption of Controlled Diets High in Fruit and Vegetables," Amer. J. Clin. Nutr. 68:1081-1087.

Caprioli et al., 1990, "Age-dependent deficits in radial maze performance in the rat: effect of chronic treatment with acetyl-L-carnitine," Prog. Neuro-Psychopharmacol. & Biol. Psychiat. 14(3):359-369.

Chandra, 2001, "Effect of vitamin and trace-element supplementation on cognitive function in elderly subjects," Nutrition 17(9):709-712.

(56) References Cited

OTHER PUBLICATIONS

Christen, 2000, "Oxidative stress and Alzheimer disease," Amer. J. Clin. Nutr. 71(2):621S-629S.
Coe, 2012, "Osteoarthritis in Dogs," http://www.vetbase.co.uk/information/osteoarthritis-dogs.php.
Cotman et al., 2002, "Brain Aging in the Canine: A Diet Enriched in Antioxidants Reduces Cognitive Dysfunction," Neurobiol. Of Aging 23(5):809-818.
Crayhon, 1998, "Real Power of Antioxidants," Total Health 20(2):27-35.
Cummings et al., 1996, "The Canine As an Animal Model of Human Aging and Dementia," Neurobiol. Of Aging 17:259-268.
Cutler, 1991, "Antioxidants and Aging," Amer. J. Clin. Nutr. 53(Suppl. 1):373S-379S.
Dictionary.com, 2012, Definition for "Prevent".
Dodd et al., 2003, "Can a Fortified Food Affect Behavioral Manifestations of Age-Related Cognitive Decline in Dogs?" Veterinary Medicine 98:396-408.
Droge, 2003, "Oxidative stress and aging," Adv. Exp. Med. Biol. 543:191-200.
Dzanis, 1994, "The Association of American Feed Control Officials Dog and Cat Food Nutrient Profiles: substantiation of nutritional adequacy of complete and balanced pet foods in the United States," J. Nutr. 124(12 Suppl):2535S-2539S.
Emmons, 1999, "Antioxidants to the Rescue," South Bend Tribune pp. 1-4.
Epinions.com, 2000, "Science Diet Senior Dry: The Healthiest on the Shelf!!!!" Epinions.com website.
Ernst, 1999, "Diet and Dementia, Is There a Link? A Systemati Review," Nutr. Neurosci. 2:1-6.
Estrada et al., 2001, "The Effects of Diet and Age on the Performance of the Landmark Discrimination Learning Task," 31st Ann. Meeting of Soc. For Neurosci., San Diego, CA 27(1):279, Abstract Biosis AN: PREV200100472166.
Frei, 1999, "Molecular and Biological Mechanisms of Antioxidant Action," FASEB J. 13:963-964.
Fryer, 1998, "Vitamin E Status and Neurodegenerative Disease," Nutritional Neurosci. 1(5):327-351.
Fuchs et al., 1994, "Antioxidant inhibition of skin inflammation induced by reactive oxidants: evaluation of the redox couple dihydrolipoate/lipoate," Skin Pharmacol. 7(5):278-284.
Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.
Gabbita et al., 1998, "Increased nuclear DNA oxidation in the brain in Alzheimer's disease," J. Neurochem. 71(5):2034-2040.
Grundman, 2000, "Vitamin E and Alzheimer disease: the basis for additional clinical trials," Amer. J. Clin. Nutr. 71(2):630S-636S.
Hagen et al., 1999, "(R)-alpha-lipoic acid-supplemented old rats have improved mitochondrial function, decreased oxidative damage, and increased metabolic rate," FASEB J. 13(2):411-418.
Han et al., 1997, "Lipoic acid increases de novo synthesis of cellular glutathione by improving cystine utilization," BioFactors 6(3):321-338.
Harman, 1961, "Prolongation of the normal lifespan and inhibition of spontaneous cancer by antioxidants," J. Gerontol. 16:247-254.
Harman, 1993, "Free Radical Theory of Aging: A Hypothesis on Pathogenesis of Senile Dementia of the Alzheimer's Type," Age 16:23-30.
Head et al., 1995, "Spatial Learning and Memory as a Function of Age in the Dog," Behavioral Neurosci. 109(5):851-858.
Information Network Village, 2011, Specialties (Agricultural Produce) http://www.invil.org/english/specialty/vegetable/potato/contents.jsp?con_no=602519&page_no=1.
International Search Report and Written Opinion in International Application No. PCT/US01/048495, mailed Jul. 30, 2002.
International Search Report and Written Opinion in International Application No. PCT/US01/049654, mailed Jul. 30, 2002.
International Search Report and Written Opinion in International Application No. PCT/US05/047192, mailed Jun. 14, 2000.
International Search Report and Written Opinion in International Application No. PCT/US06/027615, mailed Nov. 22, 2006.
International Search Report and Written Opinion in International Application No. PCT/US09/058244, mailed Dec. 14, 2009.
International Search Report and Written Opinion in International Application No. PCT/US09/068166, mailed May 7, 2010.
International Search Report and Written Opinion in International Application No. PCT/US09/068244, mailed Feb. 18, 2010.
International Search Report and Written Opinion in International Application No. PCT/US09/069686, mailed Nov. 12, 2010.
International Search Report and Written Opinion in International Application No. PCT/US10/041888, mailed Nov. 12, 2010.
Jayachandran et al., 1996, "Status of lipids, lipid peroxidation, and antioxidant systems with Vitamin C supplementation during aging in rats," J. Nutritional Biochem. 7(5):270-275.
Jones et al., 1997, "Evidence for the involvement of docosahexaenoic acid in cholinergic stimulated signal transduction at the synapse," Neurochemical Research 22(6):663-670.
Joseph et al., 2000, "Oxidative stress protection and vulnerability in aging: putative nutritional implications for intervention," Mechanisms of Ageing and Development 116(2-3):141-153.
Joseph, 2009, "Nutrition, Brain Aging, and Neurodegeneration," J. Neurosci. 29(41):12795-12801.
Kalaisel VI et al., 1998, "Effect of L-Carnitine on the Status of Lipid Peroxidation and Antioxidants in Aging Rats," J. Nutr. Biochem. 9:575-581.
Kealy et al., 2002, "Effects of diet restriction on life span and age-related changes in dogs," J. Amer. Vet. Med. Assoc. 220(9):1315-1320.
Keller et al., 1999, "4-hydroxynonenal increases neuronal susceptibility to oxidative stress," J. Neurosci. Res. 58(6):823-830.
Kim et al., 2006, "Antioxidant alpha-lipoic acid inhibits osteoclast differentiation by reducing nuclear factor-kappaB DNA binding and prevents in vivo bone resorption induced by receptor activator of nuclear factor-kappaB ligand and tumor necrosis factor-alpha," Free Radical Biol. & Med. 40(9):1483-1493.
Kolb et al., 1997, "Zum Bedarf an Vitaminen und an Ascorbinsaure beim Hund, mit Bemerkungen zur Publikation von M. Torel, TU51, 785-790, 996," Tieraerztliche Umschau 52(12):728-733.
Lee et al., 2004, "The impact of alpha-lipoic acid, coenzyme Q10 and caloric restriction on life span and gene expression patterns in mice," Free Radical Biol. Med. 36(8):1043-1057.
Leveque, 1998, "Cognitive Dysfunction in Dogs, Cats an Alzheimer's-Like Disease," J. Amer. Vet. Med. Assoc. 212(9):1351.
Liu et al., 1999, "Stress, aging, and brain oxidative damage," Neurochem. Res. 24(11):1479-1497.
Lovell et al., 1998, "Elevated 4-Hydroxynonenal in Ventricular Fluid in Alzheimer's Disease," Neurobiol. Of Aging 18:457-461.
Lovell et al., 1999, "Increased DNA oxidation and decreased levels of repair products in Alzheimer's disease ventricular CSF," J. Neurochem. 72(2):771-776.
Markesbery et al., 1998, "Four-Hydroxnonenal, a Product of Lipid Peroxidation, Is Increased in the Brain in Alzheimer's Disease," Neurobiol. Of Aging 19:33-36.
Markesbery et al., 1999, "Oxidative alterations in Alzheimer's disease," Brain Pathol. 9(1):133-146.
McGAHON et al., 1999, "Age-related changes in oxidative mechanisms and LTP are reversed by dietary manipulation," Neurobiology of Aging 20(6):643-653.
McGahon et al., 1999, "Age-related changes in LTP and antioxidant defenses are reversed by an alpha-lipoic acid-enriched diet," Neurobiology of Aging 20(6):655-664.
McGahon et al., 1999, "Age-related changes in synaptic function: analysis of the effect of dietary supplementation with omega-3 fatty acids," Neuroscience 94(1):305-314.
Melder, 1982, "Modulation of natural killer cell activity in mice after interferon induction: depression of activity and depression of in vitro enhancement by interferon," Infect. Immun. 36(3):990-995.
Milgram et al., 1994, "Cognitive Functions and Aging in the Dog: Acquisition of Nonspatial Visual Tasks," Behavioral Neurosci. 108(1):57-68.

(56) References Cited

OTHER PUBLICATIONS

Milgram et al., 1999, "Landmark Discrimination Learning in the Dog," Learning & Memory 6(1):54-61.
Milgram et al., 2000, "Landmark Discrimination Learning in Aged Dogs Is Improved by Treatment with an Antioxidant Enriched Diet," Poster Presentation No. 193.9 at Society for Neuroscience Meeting New Orleans, LA.
Milgram et al., 2001, "Age Dependent Cognitive Dysfunction in Canines: Dietary Intervention," Proc. Of the Third International Conference on Veterinary Behavioural Medicine, Overall, ed., Universities Federation for Animal Welfare, publisher pp. 53-57.
Milgram et al., 2002, "Dietary Enrichment Counteracts Age-Associated Cognitive Dysfunction in Canines," Neurobiol. Of Aging 23(5):737-745.
Milgram et al., 2002, "Landmark Discrimination Learning in the Dog: Effects of Age, an Antioxidant Fortified Food, and Cognitive Strategy," Neurosci. Biobehav. Rev. 26(6):679-695.
Milgram et al., 2004, "Long-Term Treatment with Antioxidants and a Program of Behavioral Enrichment Reduces Age-Dependent Impairment in Discrimination and Reversal Learning in Beagle Dogs," Exp. Gerontol. 39(5):753-765.
Milgram et al., 2005, "Learning Ability in Aged Beagle Dogs is Preserved by Behavioral Enrichment and Dietary Fortification: A Two-Year Longitudinal Study," Neurobiology of Aging 26(1):77-90.
Nourhashemi et al., 2000, "Alzheimer disease: protective factors," Amer. J. Clin. Nutr. 71(2):643S-649S.
Packer et al., 1995, "Alpha-Lipoic acid as a biological antioxidant," Free Radical Biol. & Med. 19(2):227-250.
Packer et al., 1997, "Neuroprotection by the metabolic antioxidant alpha-lipoic acid," Free Radical Biol. & Med. 22(1-2):359-378.
Pastuszka et al., 2007, "Alpha-lipoic acid may be a clinically useful therapy in interstitial cystitis," Medical Hypotheses 69(4):957-958.
Patrick, 2000, "Nutrients and HIV: part three—N-acetylcysteine, alpha-lipoic acid, L-glutamine, and L-carnitine," Alt. Med. Review 5(4):290-305.
Perkins et al., 1999, "Association of antioxidants with memory in a multiethnic elderly sample using the Third National Health and Nutrition Examination Survey," Amer. J. Epidemiol. 150(1):37-44.
Petsonthepark.com, 2007, "Science Diet Large Breed Senior 8kg," www.petsonthepark.com.au.prod207.htm.
Petwave.com, 2012, "Treamtment [sic] & Prognosis of Renal Dysplasia in Dogs".
Podda et al., 1994, "Alpha-lipoic acid supplementation prevents symptoms of vitamin E deficiency," Biochem. Biophys. Res. Commun 204(1):98-104.
Pratico et al., 1998, "Increased F2-isoprostanes in Alzheimer's disease: evidence for enhanced lipid peroxidation in vivo," FASEB J. 12(15):1777-1783.
Pugh et al., eds., 2000, Stedman's Medical Dictionary, 27th Edition, Williams & Wilkins, p. 377.
Radak et al., 2001, "Regular exercise improves cognitive function and decreases oxidative damage in rat brain," Neurochem. International 38(1):17-23.
Riedel et al., 1998, "Nutrients, age and cognitive function," Curr. Opin. Nutr. Metab. Care 1(6):579-585.
Rogers, 2001, "A healthy body, a healthy mind: long-term impact of diet on mood and cognitive function," Proceedings of the Nutrition Society 60(1):135-143.
Rosenberg et al., 1959, "Effect of α-lipoic acid on vitamin C and vitamin E deficiencies," Arch. Biochem. Biophys. 80(1):86-93.
Roy et al., 1998, "Redox regulation of cell functions by alpha-lipoate: biochemical and molecular aspects," BioFactors 7(3):263-267.
Roy et al., 1998, "Redox regulation of cell functions by alpha-lipoate: biochemical and molecular aspects," BioFactors 8(1-2):17-21.
Ruehl et al., 1998, "Canine Cognitive Dysfunction," Ch. 13 in: *Psychopharmacology of Animal Behavior Disorders*, Wiley-Blackwell, publisher, Dodman et al., eds., pp. 283-304.
Ruvo et al., 2000, "Nutritional antioxidants as antidegenerative agents," Int. J. Developmental Neurosci. 18(4-5):359-366.
Rybak et al., 1999, "Dose dependent protection by lipoic acid against cisplatin-induced ototoxicity in rats: antioxidant defense system," Toxicol. Sci. 47(2):195-202.
Sano et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.
Sastre et al., 1998, "A Ginkgo biloba extract (Egb 761) prevents mitochondrial aging by protecting against oxidative stress," Free Radical Biol. Med. 24(2):298-304.
Schoenherr et al., 1997, "Nutritional modification of inflammatory diseases," Seminars in Veterinary Medicine and Surgery (Small Animal) 12(3):212-222.
Schupke et al., 2001, "New metabolic pathways of alpha-lipoic acid," Drug Metab. Dispos. 29(6):855-862.
Shigenaga et al., 1994, "Oxidative damage and mitochondrial decay in aging," PNAS 91(23):10771-10778.
Siwak et al., 2000, "Age-associated changes in non-cognitive behaviors in a canine model of aging," Soc. Neurosci. 26(2):2332, Abstract No. 873.3.
Siwak et al., 2003, "Locomotor Activity Rhythms in Dogs Vary with Age and Cognitive Status," Behavioral Neurosci. 117(4):813-824.
Socci et al., 1995, "Chronic antioxidant treatment improves the cognitive performance of aged rats," Brain Research 693(1-2):88-94.
Stoll et al., 1993, "The potent free radical scavenger alpha-lipoic acid improves memory in aged mice: putative relationship to NMDA receptor deficits," Pharmacol. Biochem. & Behavior 46(4):799-805.
Stoll et al., 1994, "The potent free radical scavenger alpha-lipoic acid improves cognition in rodents," Ann. NY Acad. Sci. 717:122-128.
SYUFY, 2007, "Q. How Long Is the Common Cat Supposed to Live?" http://cats.about.com/cs/catmanagement101/f/lifespan_cats.htm website retrieved Nov. 12, 2007.
Tapp et al., 2003, "An Antioxidant Enriched Diet Improves Concept Learning in Aged Dogs," 33rd Annual Meeting of Soc. For Neurosci., New Orleans, LA Biosis AN: PREV200400205135.
Tsokos et al., 1982, "Natural killer cells and interferon responses in patients with systemic lupus erythematosus," Clin. Exp. Immunol 50(2):239-245.
Vancouver Vets, 2011, "Osteoarthritis in Dogs. Treatment & Prognosis" www.articlesbase.com/print/5146156.
Vazour, 2012, "Dietary Polyphenols as Modulators of Brain Functions: Biological Actions and Molecular Mechanisms Underpinning Their Beneficial Effects," Oxidative Med. And Cell. Longevity vol. 2012, Article ID: 914273, 16 pgs.
Villeponteau et al., 2000, "Nutraceutical interventions may delay aging and the age-related diseases," Exp. Gerontol. 35(9-10):1405-1417.
Weaver et al., 1988, "Health effects and metabolism of dietary eicosapentaenoic acid," Prog. Food Nutr. Sci. 12(2):111-150.
Youdim et al., 2000, "Essential fatty acids and the brain: possible health implications," Int. J. Devel. Neurosciences 18(4-5):383-399.

* cited by examiner

US 8,722,112 B2

METHOD FOR PROLONGING THE LIFE OF ANIMALS

CROSS-REFERENCE TO RELATED APPLICATIONS

This application claims priority to U.S. Provisional Application Ser. No. 60/699,145 filed Jul. 14, 2005, the disclosure of which is incorporated herein by reference.

FIELD OF THE INVENTION

The invention relates generally to methods for prolonging the life of animals and particularly to the use of antioxidants for prolonging the life of animals.

BACKGROUND OF THE INVENTION

Free radical-induced oxidative stress is a major factor in the long-term tissue degradation associated with aging. Living cells during their normal functions continuously produce free radicals. Free radicals are highly reactive substances capable of reacting irreversibly with many biological molecules, thus causing progressive deterioration of the biological system that eventually results in aging and death. Free radicals are normally neutralized by the body's production of antioxidant enzymes and nutrient-derived antioxidants. Numerous studies have been conducted to determine whether antioxidants can reduce oxidative stress or affect the longevity of animals. While animals currently live longer and have a better quality of life due to improved nutrition and medical care, there is still a need for new or alternative methods and compositions for increasing the longevity of animals, in particular animals that are already old.

SUMMARY OF THE INVENTION

The present invention provides methods for increasing the longevity of an animal. The methods comprise administering to the animal when the animal is old an antioxidant-comprising composition. An antioxidant-comprising composition is a composition comprising one or more antioxidants, and optionally additional ingredients. The total antioxidant amount of the one or more antioxidants in the composition is sufficient to increase the longevity of the animal.

In one embodiment, the antioxidant-comprising composition is a food composition that is administered by feeding the composition to the animal.

The invention provides an article of manufacture comprising (a) a package containing a composition that comprises one or more antioxidants in a total antioxidant amount sufficient, when administered to an old animal, to increase the longevity of the animal; and (b) a means for communicating information about or instructions for administering the composition to an old animal to increase the longevity of the animal, said communicating means being attached to or enclosed in the package.

The invention also provides a kit comprising (a) a first package containing a composition that comprises one or more antioxidants in a total antioxidant amount sufficient, when administered to an old animal, to increase the longevity of the animal; (b) a second package containing a food base; and (c) a means for communicating information about or instructions for adding the antioxidant-comprising composition to the food base and administering the resulting antioxidant-fortified composition to an old animal to increase the longevity of the animal.

A communicating means as provided in the article of manufacture or kit described above is itself a still further embodiment of the invention.

Other and further objects, features, and advantages of the present invention will be readily apparent to those skilled in the art.

DETAILED DESCRIPTION OF THE INVENTION

This detailed description is intended only to acquaint others skilled in the art with the present invention, its principles, and its practical application so that they may adapt and apply the invention in its numerous forms as best suited to the requirements of a particular use. This detailed description and its specific examples are intended for purposes of illustration only. The invention, therefore, is not limited to the embodiments described herein and may be variously modified.

The invention provides methods for increasing the longevity of animals. A method of the invention comprises administering to an old animal an antioxidant-comprising composition as more fully described herein.

The term "old" herein means relatively advanced in age, for example at least about one-third of a normal lifespan for the animal species. Thus illustratively for a domestic dog or cat of a breed having a normal life expectancy at birth of about 15 years, an "old" animal is typically one of at least about 5 years of age.

The phrases "increasing longevity" and "prolonging life" are used interchangeably herein and refer to increasing the chronological age of an animal at its death of natural causes or (only for a nonhuman animal) by euthanasia when, in the judgment of the animal's caregiver or a veterinarian, quality of life for the animal has seriously and irreversibly deteriorated. Thus in one embodiment, practice of the method of the invention can result in delaying death of an animal by natural causes. In another embodiment, practice of the invention can result in deferring a date when for humane reasons a decision has to be taken to terminate an animal's life.

The animal can be human or non-human. In various embodiments, the animal is a vertebrate, for example a fish, a bird, a reptile or a mammal. The present method is especially useful for an animal having a normal life expectancy at birth of greater than about 1 year, for example greater than about 3 years, or greater than about 5 years. Thus, for example, in one embodiment the animal is non-murine, i.e., other than a rodent of the family Muridae. Illustratively among mammals, the subject animal can be a member of the order Carnivora, including without limitation canine and feline species.

In a particular embodiment, the animal is a companion animal. A "companion animal" herein is an individual animal of any species kept by a human caregiver as a pet, or any individual animal of a variety of species that have been widely domesticated as pets, including dogs (*Canis familiaris*) and cats (*Felis domesticus*), whether or not the individual animal is kept solely or partly for companionship. Thus "companion animals" herein include working dogs, farm cats kept for rodent control, etc., as well as pet dogs and cats.

In some embodiments, the invention provides a method for increasing longevity of a canine animal such as a dog. The method comprises administering an antioxidant-comprising composition to the animal when the animal is old. In a particular embodiment, the canine is at least about 7 years old when the composition is administered. In other embodiments, the invention provides a method for increasing longevity of a feline animal such as a cat. The method comprises administering an antioxidant-comprising composition to the animal when the animal is old. In a particular embodiment, the feline is at least about 7 years old when the composition is administered. Whether canine or feline, the animal receiving the antioxidant-comprising composition can optionally be at least about 8, for example at least about 9 or at least about 10, years old. In various embodiments the canine or feline subject is a senior dog or cat, or a geriatric dog or cat, as these terms are generally used in literature pertaining to canine or feline nutrition.

Notwithstanding these illustrative embodiments, the methods of the invention are suitable for other animals, including non-human mammals such as non-human primates (e.g., monkeys, chimpanzees, etc.), companion and working animals (e.g., horses, etc.), farm animals (e.g., goats, sheep, pigs, cattle, etc.), and wild and zoo animals (e.g., wolves, bears, deer, etc.). The methods of the invention also are generally suitable for use with non-mammalian animals, such as companion, farm, zoo, and wild birds, (including, for example, song birds, parrots, ducks, geese, chickens, turkeys, ostriches, etc.). The term "animal" means a human or non-human animal, including avian, bovine, canine, equine, feline, hicrine, murine, ovine, and porcine animals. Preferably, the animal is a canine or feline.

The methods of the invention comprise administering to an animal an antioxidant-comprising composition. The total antioxidant amount of the one or more antioxidants in the composition is sufficient, upon administration of the composition to an old animal, to increase the longevity of the animal.

The composition is administered at a frequency and for a period effective to increase longevity of the animal. The phrase "a total antioxidant amount sufficient to increase the longevity of the animal" herein should be read in the context of a regimen of repeated administration at such a frequency and over such a period. Typically and most conveniently, the composition is administered at least once daily, but in certain situations less frequent, e.g., twice weekly or weekly, administration can be effective. For greatest benefit, administration should continue for a prolonged period, for example at least about 6 months, or at least about 1 year, or at least about 2 years, or at least about 3 years. In one embodiment, administration continues from a time of initiation for substantially the remainder of the animal's life.

In one embodiment, the time of initiation is at any stage of the animal's life (i.e., there is no upper or lower age limit for initiating administration), so long as at least part of the administration regimen occurs when the animal is old. In a particular embodiment, however, administration is initiated when the animal is already old. For example, in the case of canine and feline companion animals, administration can be initiated when the animal is at least about 5, at least about 6, at least about 7, at least about 8, at least about 9, or at least about 10 years old.

In some embodiments, a single antioxidant-comprising composition of the invention is administered to the animal for the entire period of administration. In other embodiments, different antioxidant-comprising compositions are administered to the animal at different times. For example, the selection and/or amounts of individual antioxidants can, if desired, vary over the period of administration.

In some embodiments, an antioxidant-comprising composition of the invention is formulated for oral administration. Illustratively, such a composition can be a food composition, a supplement, a treat or a toy, it being noted that some, but not all, supplements, treats and toys are themselves food compositions. Food compositions are administered to the animal by feeding. Where the animal is a companion animal, a food composition useful in the method of the invention is typically one that is nutritionally adapted for feeding to such an animal. A food composition so adapted is referred to herein as a "pet food". Pet foods can be more particularly adapted to the special nutritional needs of canines or felines, or to certain subpopulations thereof such as large-breed dogs, adult dogs or cats, senior dogs or cats, geriatric dogs or cats, etc.

In one embodiment, an antioxidant-comprising food composition provides a substantially nutritionally complete diet for the animal. A "nutritionally complete diet" is a diet that includes sufficient nutrients for maintenance of normal health of a healthy animal on the diet.

In another embodiment, an antioxidant-comprising food composition is a supplement, i.e., a food composition used with another food composition to improve the nutritive balance or performance of the diet as a whole. Such supplements include compositions that are fed undiluted as a supplement to other foods, offered free choice with other parts of an animal's ration that are separately available to the animal, or diluted and mixed with an animal's regular food to produce a substantially nutritionally complete diet. Supplements can alternatively be in a form other than a food composition, for example in a pharmaceutical-like dosage form including, for example, powders, liquids, syrups, pills, etc.

In yet another embodiment, an antioxidant-comprising food composition is a treat. Treats include, for example, compositions given to an animal as a reward or to entice the animal to eat during a non-meal time. Treats for dogs that are food compositions having at least some nutritional value include, for example, dog biscuits. Treats can alternatively be substantially non-nutritional (except to the extent that the one or more antioxidants therein can be considered nutrients). An antioxidant-comprising composition useful herein can itself form a treat, be coated onto an existing treat, or both.

In yet another embodiment, an antioxidant-comprising composition is a toy adapted for oral use by an animal. Toys include, for example, chewable toys, such as artificial bones for dogs. A composition useful herein can form a coating on the surface of a toy or on the surface of a component of a toy, be incorporated partially or fully throughout the toy, or both. A wide range of suitable toys is currently marketed, including partially consumable toys (e.g., toys comprising plastic components) and fully consumable toys (e.g., rawhides and various artificial bones). Toys are available for human and non-human use, particularly for companion, farm, and zoo animal use, and more particularly for dog, cat, or bird use.

In some embodiments, the antioxidant-comprising compositions useful herein are food compositions meeting the typical food intake requirements of the animal. Typical food intake requirements for old dogs and cats are shown in Table 1.

TABLE 1

Typical Adult Food Intake Requirements
(% of Diet on Dry Matter Basis)

| Food Component | Old Dogs | Old Cats |
| --- | --- | --- |
| crude protein | 15-23 | 30-45 |
| crude fat | 7-15 | 10-25 |
| crude fiber | >2 | <10 |
| calcium | 0.5-1.0 | 0.6-1.0 |
| phosphorus | 0.25-0.75 | 0.5-0.7 |
| sodium | 0.15-0.35 | 0.2-0.5 |
| magnesium | | 0.05-0.1 |

As discussed above, compositions useful herein comprise one or more antioxidants (i.e., materials that either directly quench a free radical or indirectly cause a free radical to be quenched). A variety of materials that exhibit free radical quenching or absorbing capacity can be used in the antioxidant-comprising compositions of the invention (for example, fruits, vegetables, certain vitamins, and other chemical compounds). Raw ingredients with high oxygen radical absorbing content include, for example, raw spinach pomace, raw tomato pomace, raw citrus pulp, raw grape pomace, raw carrot granules, raw broccoli, raw green tea, raw corn gluten meal, and raw rice bran. Foods or food products that exhibit free radical quenching or absorbing capacity include, for example, spinach (e.g., spinach pomace), tomato (e.g., tomato pomace), citrus fruit (e.g., citrus pulp), grape (e.g., grape pomace), carrot (e.g., carrot granules), broccoli, corn gluten meal, and rice bran. Compounds that exhibit free radical quenching or absorbing capacity include, for example, coenzyme $Q_{10}$ (ubiquinone), beta-carotene, astaxanthin (3,3'-dihydroxy-4,4'-diketo-beta-carotene), glutathione, L-carnitine, alpha-lipoic acid, lutein, lycopene, N-acetylcysteine, polyphenols, S-adenosylmethionine, selenium, soy isoflavones, taurine, tocotrienols, vitamin C, and vitamin E.

In some embodiments, a composition used in practice of the invention comprises vitamin E. The term "vitamin E" herein means any form of vitamin E suitable for consumption by an animal including, but not limited to, any tocopherol or tocotrienol compound, any enantiomer or racemate thereof, and any mixture of such compounds having vitamin E activity, e.g., $\alpha$-tocopherol (5,7,8-trimethyltocol), $\beta$-tocopherol (5,8-dimethyltocol), $\gamma$-tocopherol (7,8-dimethyltocol), $\delta$-tocopherol (8-methyltocol), $\alpha$-tocotrienol (5,7,8-trimethyltocotrienol), $\beta$-tocotrienol (5,8-dimethyltocotrienol), $\gamma$-tocotrienol (7,8-dimethyltocotrienol), and $\delta$-tocotrienol (8-methyltocotrienol). Vitamin E can be administered as any one or a mixture of the above compounds or in the form of various derivatives thereof such as esters, including vitamin E acetate, succinate, palmitate and the like, that exhibit vitamin E activity after ingestion by an animal. Typically, vitamin E as used in the present method comprises $\alpha$-tocopherol or an ester thereof. Vitamin E amounts are expressed herein as DL-$\alpha$-tocopheryl acetate equivalent amounts. Illustratively, a composition can comprise from about 100 ppm to about 2,000 ppm, for example from about 150 ppm to about 1,500 ppm, or from about 500 ppm to about 1,000 ppm, vitamin E.

In some embodiments, a composition used in practice of the invention comprises vitamin C. The term "vitamin C" herein means any form of vitamin C suitable for consumption by an animal including, but not limited to, ascorbic acid, L-ascorbic acid, and various derivatives thereof such as calcium phosphate salt, cholesteryl salt, and ascorbate-2-monophosphate. Salts of vitamin C include the sodium salt, calcium salt, zinc salt, and ferrous salt. Esters include stearate, palmitate and like derivatives. Vitamin C can be in any physical form such as a liquid, a semisolid, a solid, or a heat stable form that exhibits vitamin C activity after ingestion by an animal. Vitamin C amounts are expressed herein as ascorbic acid. Illustratively, a composition can comprise from about 25 ppm to about 10,000 ppm, for example from about 50 ppm to about 5,000 ppm, or from about 75 ppm to about 1,000 ppm, vitamin C.

In some embodiments, a composition used in practice of the invention comprises alpha-lipoic acid. Illustratively, a composition can comprise from about 25 ppm to about 600 ppm, for example from about 50 ppm to about 200 ppm, or from about 100 ppm to about 200 ppm, alpha-lipoic acid. Alpha-lipoic acid can be administered for example as an acid or lipoate derivative as described in U.S. Pat. No. 5,621,117.

In some embodiments, a composition used in practice of the invention comprises L-carnitine. Generally, compositions that are administered to cats comprise slightly higher L-carnitine amounts than the corresponding compositions for dogs. Illustratively, compositions that are administered to cats can comprise from about 100 ppm to about 5,000 ppm, for example from about 200 ppm to about 600 ppm, or from about 400 ppm to about 600 ppm, L-carnitine. Illustratively, compositions that are administered to dogs can comprise from about 50 ppm to about 5,000 ppm, for example from about 100 ppm to about 400 ppm, or from about 200 ppm to about 400 ppm, L-carnitine. L-carnitine can be administered as L-carnitine or as a derivative, for example, a salt (for example, hydrochloride), ester (for example, fumarate ester or succinate ester), or acetylated L-carnitine.

An antioxidant-comprising composition can optionally comprise one or more of beta-carotene, for example in an amount from about 1 ppm to about 15 ppm; selenium, for example in an amount from about 0.1 ppm to about 5 ppm; lutein, for example in an amount from about 5 ppm to about 15 ppm; coenzyme $Q_{10}$, for example in an amount from about 25 ppm to about 100 ppm; S-adenosylmethionine, for example in an amount from about 50 ppm to about 100 ppm; taurine, for example in an amount from about 500 ppm to about 1500 ppm; soy isoflavones, for example in an amount from about 25 ppm to about 200 ppm; N-acetylcysteine, for example in an amount from about 50 ppm to about 1600 ppm; glutathione, for example in an amount from about 50 ppm to about 250 ppm; and/or ginkgo biloba extract, for example in an amount from about 50 ppm to about 120 ppm.

In some embodiments, an antioxidant-comprising composition comprises more than one of the above-enumerated antioxidants. For example, in one embodiment, such a composition comprises vitamin E, vitamin C, L-carnitine, and alpha-lipoic acid. In one example, the composition of this embodiment comprises from about 50 ppm to about 10,000 ppm vitamin C, from about 100 ppm to about 2,000 ppm vitamin E, from about 25 ppm to about 600 ppm alpha-lipoic acid, and from about 100 ppm to about 5,000 ppm L-carnitine. In another example, the composition of this embodiment comprises from about 50 ppm to about 100 ppm vitamin C, from about 500 ppm to about 1,000 ppm vitamin E, from about 100 ppm to about 200 ppm alpha-lipoic acid, and from about 200 ppm to about 400 ppm L-carnitine.

In another embodiment, an antioxidant-comprising composition comprises vitamin E, vitamin C, L-carnitine, alpha-lipoic acid, beta-carotene, and taurine. In one example, the composition of this embodiment comprises from about 50 ppm to about 10,000 ppm vitamin C, from about 100 ppm to about 2,000 ppm vitamin E, from about 25 ppm to about 600 ppm alpha-lipoic acid, from about 100 ppm to about 5,000 ppm L-carnitine, from about 1 ppm to about 25 ppm beta-carotene, and from about 500 ppm to about 8900 ppm taurine. In another example, the composition of this embodiment comprises from about 50 ppm to about 100 ppm vitamin C, from about 500 ppm to about 1,000 ppm vitamin E, from about 100 ppm to about 200 ppm alpha-lipoic acid, from about 200 ppm to about 400 ppm, from about 5 ppm to about 15 ppm beta-carotene, and from about 1000 ppm to about 8900 ppm taurine.

In some embodiments, a food composition is modified to replace some of the composition's ingredients having low oxygen radical absorbing capacity (for example, corn) with ingredients with high oxygen radical absorbing capacity. For example, a food composition can be formulated to replace from about 1% to about 5% of the ingredients having low oxygen radical absorbing capacity with one or more of spinach pomace, tomato pomace, citrus pulp, grape pomace, carrot granules, broccoli, green tea, ginkgo biloba, and corn gluten meal.

Food compositions useful herein can be prepared in, for example, a dry, canned, wet, or intermediate moisture form using conventional pet food manufacturing processes.

In preparing a food composition, one or more antioxidants can be incorporated into the composition during processing, such as during and/or after mixing of other components of the composition. Distribution of the one or more antioxidants into the composition can be accomplished by conventional means.

In preparing an illustrative canned or wet food composition, ground animal and poultry proteinaceous tissues are mixed with other ingredients, including fish oils, cereal grains, other nutritionally balancing ingredients, special-purpose additives (e.g., vitamin and mineral mixtures, inorganic salts, cellulose and beet pulp, bulking agents, and the like); and water in an amount sufficient for processing is also added. These ingredients can be mixed in a vessel suitable for heating while blending the components. Heating of the mixture may be affected in any suitable manner, such as, for example, by direct steam injection or by using a vessel fitted with a heat exchanger. Following addition of the last ingredient, the mixture is heated to a temperature range of from about 50° F. to about 212° F., for example from about 70° F. to about 140° F. Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

Food compositions can alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

Treats can be prepared by, for example, an extrusion or baking process similar to those described above for a dry food composition. Other processes also may be used to either coat an antioxidant-comprising composition on the exterior of an existing treat form, or inject it into an existing treat form.

Toys useful herein can illustratively be prepared by coating an existing toy with an antioxidant-comprising composition.

In another embodiment of the invention, an article of manufacture comprises a package containing an antioxidant-comprising composition as described herein. Any form of package appropriate to the nature of the composition can be used, including without limitation a can, jar, pouch, bag, bag in a box, and the like. The article of this embodiment further comprises a means for communicating information about or instructions for administering the composition to an old animal to increase the longevity of the animal. The communicating means is attached to or enclosed in the package. Any suitable form of communicating means can be employed, for example a document such as a label, brochure, advertisement or package insert, a computer-readable digital or optical medium such as a diskette or CD, an audio presentation, for example on an audiotape or CD, or a visual presentation, for example on a videotape or DVD. The communicating means can refer to further information located elsewhere, such as on a website.

In yet another embodiment of the invention, a kit comprises a first package as described above containing an antioxidant-comprising composition, and a second package containing a food base. The kit of this embodiment further comprises a means for communicating information about or instructions for adding the antioxidant-comprising composition to the food base, optionally with mixing. The communicating means can specify amounts of the antioxidant-comprising composition to be added to a given amount of the food base as appropriate for particular situations. The communicating means also provides information about or instructions for administering the resulting antioxidant-fortified food composition to an old animal to increase the longevity of the animal. The communicating means can be provided together with or separately from the package, and can take any suitable form, such as those described above including one or more pages on a website.

Such a communicating means, comprising for example a document such as a label, brochure, advertisement or package insert, a computer-readable digital or optical medium such as a diskette or CD, an audio presentation, for example on an audiotape or CD, a visual presentation, for example on a videotape or DVD, and/or one or more pages on a website, is itself a still further embodiment of the invention.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

EXAMPLES

The invention can be further illustrated by the following examples of preferred embodiments, although it will be understood that these examples are included merely for purposes of illustration and are not intended to limit the scope of the invention unless otherwise specifically indicated.

Example 1

A group of twelve (12) aged beagles (average age 10.03 years) was initiated on a control food approximately the same as the one described in Table 1 above (the control food also contained approximately 100 ppm vitamin E). A second group of twelve aged beagles (average age 10.16 years) was initiated on food A, which was similar to the control food but contained approximately 950 ppm vitamin E, approximately 300 ppm L-carnitine, approximately 100 ppm alpha-lipoic acid, and approximately 80 ppm vitamin C. In addition, corn in an amount of approximately 5% of the control food was replaced in food A with approximately 1% tomato pomace, approximately 1% spinach, approximately 1% carrots, approximately 1% citrus pulp, and approximately 1% grape pomace. All dogs were fed the control food or food A for the remainder of their life. The average age at time of death of the dogs fed control food was 13.52 years. The average age at time of death for dogs fed food A was 14.21 years. Five of the dogs fed control food died before they reached thirteen years of age. None of the dogs fed food A died before the age of thirteen. The average time of survival for the dogs fed control food was 3.49 years. The average time of survival for the dogs fed food A was 4.06 years.

TABLE 2

Differences between Control Food and Food A

| Ingredient | Control food | Food A |
| --- | --- | --- |
| Vitamin E | approx. 100 ppm | approx. 950 ppm |
| Vitamin C | none detected | approx. 80 ppm |
| α-Lipoic acid | none added | approx. 100 ppm |
| L-carnitine | none added | 300 ppm |
| Spinach | none added | 1% |
| Tomato pomace | none added | 1% |
| Carrots | none added | 1% |
| Grape pomace | none added | 1% |
| Citrus pulp | none added | 1% |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for increasing the longevity of an animal comprising: administering to the animal a composition comprising antioxidants in a total antioxidant amount sufficient to increase the longevity of the animal, wherein the composition comprises 200-400 ppm L-carnitine, at least 25 ppm α-lipoic acid, at least 50 ppm vitamin C, at least 100 ppm vitamin E, at least 1% by weight of tomato pomace, dried spinach, dried carrot, dried citrus pulp, and dried grape pomace and at least one food ingredient, wherein the food ingredient is selected from the group consisting of fat, protein, fiber, and mixtures thereof, wherein the animal is a dog, and wherein the dog is at least 7 years old.

2. The method of claim 1, wherein the composition is administered to the animal for at least two years measured from a time when the animal is at least 7 years old.

3. The method of claim 1, wherein the composition is administered to the animal for the remainder of the animal's life from a time when the animal is at least 7 years old.

4. The method of claim 1, wherein the composition is a food, a supplement, a treat, or a toy.

5. The method of claim 1, wherein the composition is a nutritionally adapted food composition and is administered by feeding the food composition to the animal.

6. The method of claim 5, wherein the composition comprises vitamin C in an amount of about 50 ppm to about 10,000 ppm.

7. The method of claim 5, wherein the composition comprises vitamin C in an amount of about 50 ppm to about 100 ppm.

8. The method of claim 5, wherein the composition comprises vitamin E in an amount of about 100 ppm to about 2,000 ppm.

9. The method of claim 5, wherein the composition comprises vitamin E in an amount of about 500 ppm to about 1,000 ppm.

10. The method of claim 5, wherein the composition comprises alpha-lipoic acid in an amount of about 25 ppm to about 600 ppm.

11. The method of claim 5, wherein the composition comprises alpha-lipoic acid in an amount of about 100 ppm to about 200 ppm.

12. The method of claim 5, wherein the composition comprises L-carnitine in an amount of about 100 ppm to about 5,000 ppm.

13. The method of claim 5, wherein the composition comprises: from about 50 ppm to about 100 ppm vitamin C; from about 500 ppm to about 1,000 ppm vitamin E; and from about 100 ppm to about 200 ppm alpha-lipoic acid.

* * * * *